United States Patent [19]

Wozney et al.

[11] Patent Number: 5,106,748

[45] Date of Patent: Apr. 21, 1992

[54] DNA SEQUENCES ENCODING 5 PROTEINS

[75] Inventors: John M. Wozney, Hudson; Vicki A. Rosen, Brookline; Elizabeth A. Wang, Carlisle, all of Mass.

[73] Assignee: Genetics Institute, Inc., Cambridge, Mass.

[21] Appl. No.: 370,547

[22] Filed: Jun. 23, 1989

Related U.S. Application Data

[63] Continuation-in-part of Ser. No. 347,559, May 4, 1989, abandoned, which is a continuation-in-part of Ser. No. 329,610, Mar. 28, 1989, abandoned, which is a continuation-in-part of Ser. No. 179,100, Apr. 8, 1988, Pat. No. 5,013,649, Ser. No. 179,101, Apr. 8, 1988, abandoned, and Ser. No. 179,197, Apr. 8, 1988, each is a continuation-in-part of Ser. No. 28,285, Mar. 20, 1987, abandoned, and Ser. No. 31,346, Mar. 26, 1987, Pat. No. 4,877,864, each is a continuation-in-part of Ser. No. 943,332, Dec. 17, 1986, abandoned, and Ser. No. 880,776, Jul. 1, 1986, abandoned.

[51] Int. Cl.$^5$ .................. C07H 15/12; C12P 21/00; C12P 21/02; C12P 19/34; C12N 15/03; C12N 15/04; C12N 15/06; C12N 1/20; C12N 1/14; A61K 37/00; C07K 7/00; C07K 13/00

[52] U.S. Cl. .................. 435/252.3; 435/252.33; 435/254; 435/240.2; 435/69.1; 435/91; 435/172.3; 435/320.1; 536/27; 935/9; 935/11; 935/69; 935/70; 935/73; 935/74; 935/27

[58] Field of Search ............. 435/68, 70, 91, 172.3, 435/320, 252.3, 252.33, 254; 530/350, 300; 536/27

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/350 |
| 4,455,256 | 6/1984 | Urist | 530/350 |
| 4,468,464 | 8/1984 | Cohen et al. | 435/320 |
| 4,563,350 | 1/1986 | Nathan | 424/95 |
| 4,608,199 | 8/1986 | Caplan et al. | 530/414 |
| 4,619,989 | 10/1986 | Urist | 530/417 |
| 4,627,982 | 12/1986 | Seyedin et al. | 424/95 |
| 4,681,763 | 7/1987 | Nathanson | 424/95 |
| 4,727,028 | 2/1988 | Santerre et al. | 435/240.2 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/350 |
| 4,789,732 | 12/1988 | Urist | 530/350 |
| 4,795,804 | 1/1989 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |

FOREIGN PATENT DOCUMENTS

| | | |
|---|---|---|
| 336760 | 6/1989 | European Pat. Off. |
| WO89/09787 | 10/1989 | PCT Int'l Appl. |
| WO89/09788 | 10/1989 | PCT Int'l Appl. |
| WO90/03733 | 4/1990 | PCT Int'l Appl. |
| 8800205 | 1/1988 | World Int. Prop. O. |

OTHER PUBLICATIONS

Wozney et al., 1988, Science 242, 1528–1534.
Urist et al., Science, 220:680–686 (1983).
Sampath et al., Proc. Natl. Acad Sci 84: 7109–7113 (1987).

Primary Examiner—Elizabeth C. Weimar
Assistant Examiner—Christopher S. F. Low
Attorney, Agent, or Firm—Ellen J. Kapinos; Bruce M. Eisen

[57] ABSTRACT

Purified BMP-5 proteins and processes for producing them are disclosed. The proteins may be used in the treatment of bone and/or cartilage defects and in wound healing and related tissue repair.

4 Claims, 8 Drawing Sheets

FIGURE 1

1 TCTAGAGGTGAGAGCAGCCAACAAGAGAAAAAATCAAAACGCAATAAATCGGCTCTCAT 61
  LeuGluValArgAlaAlaAsnLysArgLysAsnGlnAsnArgAsnLys<u>SerGlySerHis</u>
       (1)                                       (15)

62 CAGGACTCCTCTAGAATGTCCAGTGTTGGAGATTATAACACCAGTGAACAAAAACAAGCC 121
  <u>GlnAspSerSerArg</u>MetSerSerValGlyAspTyrAsnThrSerGluGlnLysGlnAla
          (23)

122 TGTAAAAAGCATGAACTCTATGTGAGTTTCCGGGATCTGGGATGGCAGGACTGGATTATA 181
  CysLysLys<u>HisGluLeuTyrValSerPhe</u>ArgAspLeuGlyTrpGlnAspTrpIleIle
         (42)

182 GCACCAGAAGGATATGCTGCATTTTATTGTGATGGAGAATGTTCTTTTCCACTCAATGCC 241
  AlaProGluGlyTyrAlaAlaPheTyrCysAspGlyGluCysSerPheProLeuAsnAla

242 CATATGAATGCCACCAATCATGCCATAGTTCAGACTCTGGTTCACCTGATGTTTCCTGAC 301
  HisMetAsnAlaThrAsnHisAlaIleValGlnThrLeuValHisLeuMetPheProAsp

302 CACGTACCAAAGCCTTGCTGCGCGACAAACAAACTAAATGCCATCTCTGTGTTGTACTTT 361
  HisValProLysProCysCysAlaThrAsnLysLeuAsnAlaIleSerValLeuTyrPhe

362 GATGACAGCTCCAATGTCATTTTGAAAAAGTACAGAAATATGGTCGTGCGTTCGTGTGGT 421
  AspAspSerSerAsnValIleLeuLysLysTyrArgAsnMetValValArgSerCysGly

422 TGCCACTAATAGTGCATAATAATGGTAATAAGAAAAAAGATCTGTATGGAGGTTTATGA 481
  CysHisEnd (140)
481 CTACAATAAAAAAATATCTTTCGGATAAAAGGGGAATTTAATAAAATTAGTCTGGCTCATT 540

541 TCATCTCTGTAACCTATGTACAAGAGCATGTATATAGT 578

FIGURE 2

|   | 9 | 18 | 27 | 36 | 45 | 5 |
|---|---|---|---|---|---|---|
| CTG | CTG GGC | ACG CGT GCT | GTG TGG GCC | TCA GAG GCG | GGC TGG CTG | GAG TTT GAC |
| Leu (1) | Leu Gly | Thr Arg Ala | Val Trp Ala | Ser Glu Ala | Gly Trp Leu | Glu Phe Asp |

```
                  9           18           27           36           45            5
CTG CTG GGC ACG CGT GCT GTG TGG GCC TCA GAG GCG GGC TGG CTG GAG TTT GAC
Leu Leu Gly Thr Arg Ala Val Trp Ala Ser Glu Ala Gly Trp Leu Glu Phe Asp
(1)
                 63          72          81           90           99          108
ATC ACG GCC ACC AGC AAC CTG TGG GTC CTG ACT CCG CAG CAC AAC ATG GGG CTG
Ile Thr Ala Thr Ser Asn Leu Trp Val Leu Thr Pro Gln His Asn MET Gly Leu 117         126         135          144          153         162
CAG CTG AGC GTG GTC ACG CGT GAT GGG CTC AGC ATC AGC CCT GGG GCC GCG GGC
Gln Leu Ser Val Val Thr Arg Asp Gly Leu Ser Ile Ser Pro Gly Ala Ala Gly 171         180         189          198          207         216
CTG GTG GGC AGG GAC GGC CCC TAC GAC AAG CAG CCC TTC ATG GTG GCC TTC TTC
Leu Val Gly Arg Asp Gly Pro Tyr Asp Lys Gln Pro Phe MET Val Ala Phe Phe 225         234         243          252          261         270
AAG GCC AGT GAG GTC CAC GTG CGC AGT GCC CGG TCG GCC CCC GGG CGG CGC CGG
Lys Ala Ser Glu Val His Val Arg Ser Ala Arg Ser Ala Pro Gly Arg Arg Arg 279         288         297          306          315         324
CAG CAG GCC CGG AAC CGC TCC ACC CCG GCC CAG GAC GTG TCG CGG GCC TCC AGC
Gln Gln Ala Arg Asn Arg Ser Thr Pro Ala Gln Asp Val Ser Arg Ala Ser Ser 333         342         351          360          369         378
GCC TCA GAC TAC AAC AGC AGC GAG CTG AAG ACG GCC TGC CGG AAG CAT GAG CTC
Ala Ser Asp Tyr Asn Ser Ser Glu Leu Lys Thr Ala Cys Arg Lys His Glu Leu 387         396         405          414          423         432
TAC GTG AGC TTC CAG GAC CTG GGG TGG CAG GAC TGG ATC ATT GCC CCC AAG GGC
Tyr Val Ser Phe Gln Asp Leu Gly Trp Gln Asp Trp Ile Ile Ala Pro Lys Gly 441         450         459          468          477         486
TAC GCT GCC AAC TAC TGT GAC GGA GAA TGT TCG TTC CCT CTC AAC GCA CAC ATG
Tyr Ala Ala Asn Tyr Cys Asp Gly Glu Cys Ser Phe Pro Leu Asn Ala His MET 495         504         513          522          531         540
AAC GCT ACC AAC CAT GCC ATC GTG CAG ACC CTG GTT CAC CTC ATG AAC CCC GAG
Asn Ala Thr Asn His Ala Ile Val Gln Thr Leu Val His Leu MET Asn Pro Glu 549         558         567          576          585         594
TAC GTC CCC AAA CCG TGC TGC GCG CCC ACG AAA CTG AAC GCC ATC TCG GTG CTC
Tyr Val Pro Lys Pro Cys Cys Ala Pro Thr Lys Leu Asn Ala Ile Ser Val Leu 603         612         621          630          639         648
TAC TTC GAC GAC AAC TCC AAT GTC ATC CTG AAG AAG TAC CGG AAC ATG GTC GTA
Tyr Phe Asp Asp Asn Ser Asn Val Ile Leu Lys Lys Tyr Arg Asn MET Val Val
```

FIGURE 2 (CONTINUED)

```
        657         666        676        686        696        706         716
CGA GCG TGT GGG TGC CAC TGACTCGGGG TGAGTGGCTG GGGACGCTGT GCACACACTG CCTGGACTCC
Arg Ala Cys Gly Cys His
                        (222)

726         736        746        756        766        776         786
TGGATCACGT CCGCCTTAAG CCCACAGAGG CCCCCGGGAC ACAGGAGGAG ACCCCGAGGC CACCTTCGGC 796         806        816        826        836        846         856
TGGCGTTGGC CTTTCCGCCC AACGCAGACC CGAAGGGACC CTGTCCGCCC CTTGCTCACA CCGTGAGCGT 866         876        886
TGTGAGTAGC CATCGGGCTC TAGGAAGCAG CACTCGAG
```

FIGURE 3

```
         9              18             27            36            45              54
CCA ACC AAA TTA AAT GCC ATC TCT GTT CTG TAC TTT GAT GAC AGC TCC AAT GTC
Pro Thr Lys Leu Asn Ala Ile Ser Val Leu Tyr Phe Asp Asp Ser Ser Asn Val
(1)

63             72            81            90            99
ATT TTG AAA AAA TAT AGA AAT ATG GTA GTA CGC TCA TGT GGC TGC CAC
Ile Leu Lys Lys Tyr Arg Asn MET Val Val Arg Ser Cys Gly Cys His
                                                            (34)

112        122        132        142        152        162
TAATATTAAA TAATATTGAT AATAACAAAA AGATCTGTAT TAAGGTTTAT GGCTGCAATA 172        182        192
AAAAGCATAC TTTCAGACAA ACAGAAAAAA AAA
```

FIGURE 4

```
         10         20         30         40         50
CTGGTATATT TGTGCCTGCT GGAGGTGGAA TTAACAGTAA GAAGGAGAAA 60         70         80         90        100
GGGATTGAAT GGACTTACAG GAAGGATTTC AAGTAAATTC AGGGAAACAC 110        120        130        140        150
ATTTACTTGA ATAGTACAAC CTAGAGTATT ATTTTACACT AAGACGACAC 160        170        180        190        200
AAAAGATGTT AAAGTTATCA CCAAGCTGCC GGACAGATAT ATATTCCAAC 210        220        230        240        250
ACCAAGGTGC AGATCAGCAT AGATCTGTGA TTCAGAAATC AGGATTTGTT 260        270        280        290        300
TTGGAAAGAG CTCAAGGGTT GAGAAGAACT CAAAAGCAAG TGAAGATTAC 310        320        330        340        350
TTTGGGAACT ACAGTTTATC AGAAGATCAA CTTTTGCTAA TTCAAATACC 360        370        380        390        400
AAAGGCCTGA TTATCATAAA TTCATATAGG AATGCATAGG TCATCTGATC 410        420        430        440        450
AAATAATATT AGCCGTCTTC TGCTACATCA ATGCAGCAAA AACTCTTAAC 460        470        480        490        500
AACTGTGGAT AATTGGAAAT CTGAGTTTCA GCTTTCTTAG AAATAACTAC 510        520        530        540        550
TCTTGACATA TTCCAAAATA TTTAAAATAG GACAGGAAAA TCGGTGAGGA 560        570        580        590        600
TGTTGTGCTC AGAAATGTCA CTGTCATGAA AAATAGGTAA ATTGTTTTT 610        620        630        640        650
TCAGCTACTG GGAAACTGTA CCTCCTAGAA CCTTAGGTTT TTTTTTTTT 660        670        680        690        700
AAGAGGACAA GAAGGACTAA AAATATCAAC TTTTGCTTTT GGACAAAA
```

FIGURE 4 (CONTINUED)

```
701           710           719           728           737
ATG CAT CTG ACT GTA TTT TTA CTT AAG GGT ATT GTG GGT TTC CTC
MET His Leu Thr Val Phe Leu Leu Lys Gly Ile Val Gly Phe Leu
(1)

746           755           764           773           782
TGG AGC TGC TGG GTT CTA GTG GGT TAT GCA AAA GGA GGT TTG GGA
Trp Ser Cys Trp Val Leu Val Gly Tyr Ala Lys Gly Gly Leu Gly 791           800           809           818           827
GAC AAT CAT GTT CAC TCC AGT TTT ATT TAT AGA AGA CTA CGG AAC
Asp Asn His Val His Ser Ser Phe Ile Tyr Arg Arg Leu Arg Asn 836           845           854           863           872
CAC GAA AGA CGG GAA ATA CAA AGG GAA ATT CTC TCT ATC TTG GGT
His Glu Arg Arg Glu Ile Gln Arg Glu Ile Leu Ser Ile Leu Gly 881           890           899           908           917
TTG CCT CAC AGA CCC AGA CCA TTT TCA CCT GGA AAA ATG ACC AAT
Leu Pro His Arg Pro Arg Pro Phe Ser Pro Gly Lys Gln Ala Ser 926           935           944           953           962
CAA GCG TCC TCT GCA CCT CTC TTT ATG CTG GAT CTC TAC AAT GCC
Ser Ala Pro Leu Phe MET Leu Asp Leu Tyr Asn Ala MET Thr Asn 971           980           989           998           1007
GAA GAA AAT CCT GAA GAG TCG GAG TAC TCA GTA AGG GCA TCC TTG
Glu Glu Asn Pro Glu Glu Ser Glu Tyr Ser Val Arg Ala Ser Leu 1016          1025          1034          1043          1052
GCA GAA GAG ACC AGA GGG GCA AGA AAG GGA TAC CCA GCC TCT CCC
Ala Glu Glu Thr Arg Gly Ala Arg Lys Gly Tyr Pro Ala Ser Pro 1061          1070          1079          1088          1097
AAT GGG TAT CCT CGT CGC ATA CAG TTA TCT CGG ACG ACT CCT CTG
Asn Gly Tyr Pro Arg Arg Ile Gln Leu Ser Arg Thr Thr Pro Leu 1106          1115          1124          1133          1142
ACC ACC CAG AGT CCT CCT CTA GCC AGC CTC CAT GAT ACC AAC TTT
Thr Thr Gln Ser Pro Pro Leu Ala Ser Leu His Asp Thr Asn Phe 1151          1160          1169          1178          1187
CTG AAT GAT GCT GAC ATG GTC ATG AGC TTT GTC AAC TTA GTT GAA
Leu Asn Asp Ala Asp MET Val MET Ser Phe Val Asn Leu Val Glu 1196          1205          1214          1223          1232
AGA GAC AAG GAT TTT TCT CAC CAG CGA AGG CAT TAC AAA GAA TTT
Arg Asp Lys Asp Phe Ser His Gln Arg Arg His Tyr Lys Glu Phe
```

FIGURE 4 (CONTINUED)

```
1241           1250           1259           1268           1277
 CGA TTT GAT CTT ACC CAA ATT CCT CAT GGA GAG GCA GTG ACA GCA
 Arg Phe Asp Leu Thr Gln Ile Pro His Gly Glu Ala Val Thr Ala 1286           1295           1304           1313           1322
 GCT GAA TTC CGG ATA TAC AAG GAC CGG AGC AAC AAC CGA TTT GAA
 Ala Glu Phe Arg Ile Tyr Lys Asp Arg Ser Asn Asn Arg Phe Glu 1331           1340           1349           1358           1367
 AAT GAA ACA ATT AAG ATT AGC ATA TAT CAA ATC ATC AAG GAA TAC
 Asn Glu Thr Ile Lys Ile Ser Ile Tyr Gln Ile Ile Lys Glu Tyr 1376           1385           1394           1403           1412
 ACA AAT AGG GAT GCA GAT CTG TTC TTG TTA GAC ACA AGA AAG GCC
 Thr Asn Arg Asp Ala Asp Leu Phe Leu Leu Asp Thr Arg Lys Ala 1421           1430           1439           1448           1457
 CAA GCT TTA GAT GTG GGT TGG CTT GTC TTT GAT ATC ACT GTG ACC
 Gln Ala Leu Asp Val Gly Trp Leu Val Phe Asp Ile Thr Val Thr 1466           1475           1484           1493           1502
 AGC AAT CAT TGG GTG ATT AAT CCC CAG AAT AAT TTG GGC TTA CAG
 Ser Asn His Trp Val Ile Asn Pro Gln Asn Asn Leu Gly Leu Gln 1511           1520           1529           1538           1547
 CTC TGT GCA GAA ACA GGG GAT GGA CGC AGT ATC AAC GTA AAA TCT
 Leu Cys Ala Glu Thr Gly Asp Gly Arg Ser Ile Asn Val Lys Ser 1556           1565           1574           1583           1592
 GCT GGT CTT GTG GGA AGA CAG GGA CCT CAG TCA AAA CAA CCA TTC
 Ala Gly Leu Val Gly Arg Gln Gly Pro Gln Ser Lys Gln Pro Phe 1601           1610           1619           1628           1637
 ATG GTG GCC TTC TTC AAG GCG AGT GAG GTA CTT CTT CGA TCC GTG
 MET Val Ala Phe Phe Lys Ala Ser Glu Val Leu Leu Arg Ser Val 1646           1655           1664           1673           1682
 AGA GCA GCC AAC AAA CGA AAA AAT CAA AAC CGC AAT AAA TCC AGC
 Arg Ala Ala Asn Lys Arg Lys Asn Gln Asn Arg Asn Lys Ser Ser
                                                      (329)

1691           1700           1709           1718           1727
 TCT CAT CAG GAC TCC TCC AGA ATG TCC AGT GTT GGA GAT TAT AAC
 Ser His Gln Asp Ser Ser Arg MET Ser Ser Val Gly Asp Tyr Asn
         (337)
```

FIGURE 4 (CONTINUED)

```
1736           1745           1754           1763           1772
ACA AGT GAG CAA AAA CAA GCC TGT AAG AAG CAC GAA CTC TAT GTG
Thr Ser Glu Gln Lys Gln Ala Cys Lys Lys His Glu Leu Tyr Val
                                         (356)

1781           1790           1799           1808           1817
AGC TTC CGG GAT CTG GGA TGG CAG GAC TGG ATT ATA GCA CCA GAA
Ser Phe Arg Asp Leu Gly Trp Gln Asp Trp Ile Ile Ala Pro Glu
(362)

1826           1835           1844           1853           1862
GGA TAC GCT GCA TTT TAT TGT GAT GGA GAA TGT TCT TTT CCA CTT
Gly Tyr Ala Ala Phe Tyr Cys Asp Gly Glu Cys Ser Phe Pro Leu 1871           1880.          1889           1898           1907
AAC GCC CAT ATG AAT GCC ACC AAC CAC GCT ATA GTT CAG ACT CTG
Asn Ala His MET Asn Ala Thr Asn His Ala Ile Val Gln Thr Leu 1916           1925           1934           1943           1952
GTT CAT CTG ATG TTT CCT GAC CAC GTA CCA AAG CCT TGT TGT GCT
Val His Leu MET Phe Pro Asp His Val Pro Lys Pro Cys Cys Ala 1961           1970           1979           1988           1997
CCA ACC AAA TTA AAT GCC ATC TCT GTT CTG TAC TTT GAT GAC AGC
Pro Thr Lys Leu Asn Ala Ile Ser Val Leu Tyr Phe Asp Asp Ser 2006           2015           2024           2033           2042
TCC AAT GTC ATT TTG AAA AAA TAT AGA AAT ATG GTA GTA CGC TCA
Ser Asn Val Ile Leu Lys Lys Tyr Arg Asn MET Val Val Arg Ser
                                                         (450)

2051        2060         2070         2080         2090         2100
TGT GGC TGC CAC TAATATTAAA TAATATTGAT AATAACAAAA AGATCTGTAT
Cys Gly Cys His 2110         2120         2130         2140         2150
TAAGGTTTAT GGCTGCAATA AAAAGCATAC TTTCAGACAA ACAGAAAAAA AAA
```

1

DNA SEQUENCES ENCODING 5 PROTEINS

CROSS REFERENCE TO RELATED APPLICATIONS

This application is a continuation-ino-art of U.S. Ser. No. 347,539 filed 4 May 1989, now abandoned, which is a continuation-in-part of U.S. Ser. No. 329,610 filed 28 Mar. 1989, now abandoned, which is a continuation-in-part of U.S. Ser. Nos. 179,100 now U.S. Ser. No. 5,013,649; and U.S. Pat. No. 179,197 filed 8 Apr. 1988 which are continuations-in-part of U.S. Ser. Nos. 028,285 filed Mar. 20, 1987 now abandoned and U.S. Pat. No. 031,346 filed Mar. 26, 1987 now U.S. Pat. No. 4,877,864 which are continations-in-part of U.S. Ser. Nos. 943,332 filed Dec. 17, 1986 now abandoned and U.S. Pat. No. 880,776 filed July 1, 1986 now abandoned.

The present invention relates to a family of purified proteins, termed BMP-5 proteins (wherein BMP is bone morphogenic protein), which exhibit the ability to induce cartilage and/or bone formation and processes for obtaining them. These proteins may be used to induce bone and/or cartilage formation and in wound healing and tissue repair.

The invention provides human BMP-5 proteins, substantially free from other proteins with which they are co-produced, characterized by containing the amino acid sequence set forth in Table III from amino acid #1 to amino acid #34 encoded for by the DNA sequence of Table III from nucleotide #1 to nucleotide #102. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein reveals a region of approximately 14,000–20,000 daltons. It is contemplated that these proteins are capable of stimulating promoting, or otherwise inducing cartilage and/or bone formation.

The invention further provides bovine BMP-5 proteins characterized by containing the amino acid sequence set forth in Table I from at least amino acid #42 to amino acid #140 encoded for by the DNA sequence of Table I. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein reveals a region of approximately 14,000–20,000 daltons. It is contemplated that these proteins are capable of inducing cartilage and/or bone formation. Human BMP-5 proteins of the invention may be produced by culturing a cell transformed with a DNA sequence containing the nucleotide sequence the same or substantially the same as shown in Table III from nucleotide #1 to nucleotide #102, recovering and purifying from the culture medium a protein containing the amino acid sequence the same or substantially the same as shown in Table III from amino acid #1 to amino acid #34. Bovine proteins of the invention may be produced by culturing a cell transformed with a DNA sequence containing the nucleotide sequence the same or substantiallly the same as that shown in Table I from nucleotide #8 through nucleotide #427 and recovering and purifying from the culture medium a proteincontaining the amino acid sequence or a portion thereof as shown in Table I from amino acid #42 to amino acid #140.

The invention further provides a method wherein the proteins described above are utilized for obtaining realted human protein/s or other mammalian cartilage and/or bone growth protein/s. Such methods are known to those skilled in the art of genetic engineering. One method for obtaining such proteins involves utilizing the human BMP-5 coding sequence from nucleotide #1–#102 as a probe for screening human genomic and/or cDNA libraries to isolate the human genomic and/or cDNA sequence. Similar methods may employ the bovine and human BMP-5 proteins of the invention to obtain other mammalian BMP-5 cartilage and/or bone growth proteins.

These proteins are produced by culturing a cell transformed with the DNA identified as in the method described above which DNA hybridizes under stringent conditions to the nucleotide sequence substantially as shown in Table I from nucleotide #8 to nucleotide #427 or the nucleotide sequence substantially as shown in Table III comprising nucleotide #1 to #102 and which encodes a protein exhibiting cartilage and/or bone formation activity and recovering and purifying from the culture medium a protein substantially free from other proteinaceous with which it is co-produced.

The proteins of the invention may be further characterized by the ability to demonstrate cartilage and/or bone formation activity in the rat bone formation assay described below. It is further contemplated that the proteins of the invention demonstrate activity in this rat bone formation assay at a concentration of $0.5\mu$–$100\mu g$/gram of bone. It is further contemplated that these proteins demonstrate activity in this assay at a concentration of $1\mu$-g $50\mu g$/gram bone. More particularly, it is contemplated these proteins may be characterized by the ability of $1\mu g$ of the protein to score at least +2 in the rat bone formation assay.

Another aspect of the invention provides pharmaceutical compositions containing a therapeutically effective amount of a protein of the invention in a pharmaceutically acceptable vehicle or carrier. The compositions of the invention may be used to induce bone and/ or cartilage formation. These compositions may also be used for wound healing and tissue repair. Further compositions of the invention may include in addition to a BMP-5 protein of the present invention at least one other therapeutically useful agent such as the proteins designated BMP-1, BMP-2A and -2B, BMP-3, BMP-6, and BMP-7 disclosed respectively in co-owned U.S. Pat. applications Ser. No. 179,101, Ser. No. 179,100, and Ser. No. 179,197, Ser. No. 07/370,544 filed June 22, 1989, and Ser. No. 07/370,549 filed June 22, 1989. Other therapeutically useful agents include growth factors such as epidermal growth factor (EGF), fibroblast growth factor (FGF), and transforming growth factors (TGF-$\alpha$ and TGF-$\beta$). The compositions of the invention may also include an appropriate matrix, for instance, for supporting the composition and/or providing a surface for bone and/or cartilage growth.

The compositions may be employed in methods for treating a number of bone and/or cartilage defects, and periodontal disease. They may also be employed in methods for treating various types of wounds and in tissue repair. These methods, according to the invention, entail administering to a patient needing such bone and/or cartilage formation, wound healing or tissue repair, a therapeutically effective amount of a protein of the invention. These methods may also entail the administration of a protein of the invention in conjunction with at least one of the "BMP" proteins disclosed in the co-owned applications described above. In addition, these methods may also include the administration of a protein of the invention with other growth factors including EGF, FGF, TGF-α, and TGF-β.

Still a further aspect of the invention are DNA sequences coding for expression of a protein of the invention. Such sequences include the sequence of nucleotides in a 5' to 3' direction illustrated in Table I or Table III or DNA sequences which hybridize under stringent conditions with the DNA sequence of Table I or Table III and encode a protein demonstrating ability to induce cartilage and/or bone formation in the rat bone formation assay described below. It is contemplated that these proteins demonstrate activity in this assay at a concentration of 0.5μg -100μg/gram of bone. It is further contemplated that the proteins demonstrate activity in this assay at a concentration of 1μg-50μg/gram bone. More particularly, it is contemplated that these proteins demonstrate the ability of 1μg of the protein to score at least +2 in the rat bone formation assay. Finally, allelic or other variations of the sequences of Table I and III whether such nucleotide changes result in changes in the peptide sequence or not, are also included in the present invention A further aspect of the invention provides a vector containing a DNA sequence as described above in operative association with an expression control sequence therefor These vectors may be employed in a novel process for producing a protein of the invention in which a cell line transformed with a DNA sequence directing expression of a protein of the invention in opertive association with an expression control sequence therefor, is cultured in a suitable culture medium and a protein of the invention is isolated and purified therefrom. This calimed process may employ a number of known cells, both prokaryotic and eukaryotic, as host cells for expression of the polypeptide.

Other aspcts and advantages of the present invention will be apparent upon consideration of the following detailed description and preferred embodiments thereof.

BRIEF DESCRIPTION OF THE DRAWING

FIG. 1 comprises DNA sequence and derived amino acid sequence of bovine BMP-5. FIG. 1 corresponds to Table I further described below.

FIG. 2 comprises DNA sequence and derived amino acid sequence of bovine BMP-6. FIG. 2 corresponds to Table II further described below.

FIG. 3 comprises DNA sequence and derived amino acid sequence of human BMP-5 from lambda U2-16 ATCC #68019. FIG. 3 corresponds to Table II further described below.

FIG. 4 comprises full DNA sequence and derived amino acid sequence of human BMP-5 form lambda U2-16 ATCC #68019. FIG. 4 corresponds to Table IV further described below.

DETAILED DESCRIPTION OF THE INVENTION

A purified BMP-5 human cartliage/bone protein of the present invention is produced by culturing a host cell transformed with a DNA sequence comprising the DNA sequence as shown in Table III from nucleotide #1 to nucleotide #102 or substantially homologous sequences operatively linked to a heterologous regulatory control sequence and recovering, isolating and pruifying from the culture medium a protein containing the aminoa cid sequence as shown in Table III from amino acid #1 to amino acid #34 or a substantially homologous sequence. A purified BMP-5 bovine cartliage/bone protein of the present invention is produced by culturing a host cell transformed with a DNA sequence which contains the DNA sequence as shown in Table I comprising nucleotide #8 to nucleotide #427 or substantially homologous sequences and recovering from the culture medium a protein containing the amino acid sequence substantially as shown in Table I from amino acid #42 to amino acid #140 or a substantially homologous sequence.

These proteins may be further characterized by the ability to demonstrate cartliage and/or bone formation activity in the rat bone formation assay as described in Example III. It is further contemplated that these proteins demonstrate activity in the assay at a concentration of 0.5μg -100μg/gram of bone formed. It is further contemplated that these proteins demonstrate activity in this assay at a concentration of 1μg-50μg/gram bone. The proteins may be further characterized by the ability of 1μg to score at least 2 in this assay.

The proteins provided herein also include factors encoded by the sequences similar to those of Table I and Table III but into which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of Table I or Table III are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein involve modifications of the glycosylation sites. The absence of glycosylation or only partial glycosylation results from amino acid substitution or deletion at the asparagine-linked glycosylation recognition sites present in the sequences of the proteins of the invention, for example, as shown in Table I or Table III. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for the proteins of the invention. These DNA sequences include those depicted in Tables I and III in a 5' to 3' direction. Further included are those sequences which hybridize under stringent hybridization conditions [see, T. Maniatis et.al., *Molecular Cloning (A Laboratory Manula*), Cold Spring Harbor Laboratory (1982), pages 387 to 389] to the DNA sequence of Table I or Table III and demonstrate cartilage and/or bone formation activity in the rat bone formation assay. An example of one such stringent hybridization condition is hybridization at 4×SSC at 65° C., followed by a washing in 0.1×SCC at 65° C. for an hour. Alternatively, an examplary stringent hybridization condition is in 50% formamide, 4×SCC at 42° C.

Similarly, DNA sequences which encode proteins similar to the protein encoded by the sequence of Table I or Table III, but which differ in codon sequence due to the degeneracies of the genetic code or allelic variations (naturally-occurring base changes in the species population which may or may not result in an amino acid change) also encode the proteins of the invention described herein. Variations in the DNA sequences of Table I and Table III which are caused by point mutations or by induced modifications (including insertion, deletion, and substitution) to enhance the activity, half-life or production of the polypeptides encoded thereby are also encompassed in the invention.

In a further aspect, the invention provides a method for obtaining related human proteins or other mammalian BMP-5 proteins. One method for obtaining such proteins entails, for instance, utilizing the human BMP-5 coding sequence disclosed herein to probe a human genomic library using standard techniques for the human gene or fragments thereof. Sequences thus thus identified may also be used as probes to identify a human cell line or tissue which synthesizes the analogous cartilage/bone protein. A cDNA library is synthesized and screened with probes derived from the human or bovine coding sequences. The human sequence thus identified is transformed into a host cell, the host cell is cultured and the protein recovered, isolated and purified from the culture medium. The purified protein is predicted to exhibit cartilage and/or bone formation activity in the rat bone formation assay of Example III.

Another aspect of the present invention provides a novel method for producing the proteins of the invention. The method of the present invention involves culturing a suitable cell line, which has been transformed with a DNA sequence coding for expression of a protein of the invention, under the control of known regulatory sequences. The transformed cells are cultured and the BMP-5 proteins expressed thereby are recovered and purified from the culture medium using purification techniques known to those skilled in the art.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et.al., *Mol. Cell. Biol.*, 5(7):1750–1759 (1985) or Howley et.al., U.S. Pat. No. 4,419,446. Another suitable mammalian cell line, which is described in the accompanying examples, is the monkey COS-1 cell line. The mammalian cell CV-1 may also be suitable Bacterial cells may also be suitable hosts For example, the various strains of *E. coli* (e.g., HB101, MC1061) are well-known as host cells in the field of biotechnology. Various strains of *B. subtilis, Pseudomonas,* other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et.al., *Genetic Egnineering,* 8:277–298 (Plenum Press 1986) and references cited therein.

Another aspect of the present invention provides vectors for use in the method of expression of the proteins of the invention. Preferably the vectors contain the full novel DNA sequences described above which code for the novel cartilage/bone proteins of the invention. Additionally the vectors also contain appropriate expression control sequences pe rm itting exp ression of the protein sequences. Alternatively, vectors incorporating modified sequences as described above are also embodiments of the present invention and useful in the production of the proteins of the invention. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art and may be selected depending upon the selected host cells. Such selection is routine and does not form part of the present invention Host cells transformed with such vectors and progeny thereof for use in producing cartilage/bone proteins are also provided by the invention.

A protein of the present invention, which induces cartilage and/or bone formation in circumstances where bone and/or cartilage is not normally formed, has application in the healing of bone fractures and cartilage defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair).

A further aspect of the invention is a therapeutic method and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the proteins of the invention in admixture with a pharmaceutically acceptable vehicle, carrier or matrix. It is expected that the proteins of the invention may act in concert with or perhaps synergistically with one another or with other related proteins and growth factors Therapeutic methods and compositions of the invention therefore comprise one or more of the proteins of the present invention. Further therapeutic methods and compositions of the invention therefore comprise a therapeutic amount of at least one protein of the invention with a therapeutic amount of at least one of the other "BMP" proteins disclosed in co-owned and co-pending U.S. applications described above. Such methods and compositions of the invention may comprise proteins of the invention or portions thereof in combination with the above-mentioned "BMP" proteins or portions thereof. Such combination may comprise individual molecules from each of the proteins or heteromolecules formed by portions of the respective proteins For example, a method and composition of the invention may comprise a protein of the invention or a portion thereof linked with a portion of a "BMP" protein to form a heteromolecule Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), growth factors (TGF-α and TGF-β), and insulin-like growth factor (IGF). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone growth factor proteins. Domestic animals and thoroughbred horses in addition to humans are desired patients for such treatment with the proteins of the present invention The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition would include a matrix capable of delivering the cartilage/bone proteins of the invention to the site of bone and/or cartilage damage, providing a structure for the developing bone and cartilage and optimally capable of being resorbed into the body. Such matrices may be formed of materials presently in use for other implanted medical applications.

The cho ice o f mat rix mate rial is based o n biocompatibility, biodegradability, mechanical properties, cosmetic appearance and interface properties. The particular application of the compositions of the invention will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen Further matrices are comprised of pure proteins or extracellular matrix components. Other potential matrices are nonbiodegradable and chemically defined, such as sintered hydroxyapatite, bioglass, aluminates, or other ceramics Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound type of damaged tissue, the patient's age, sex, and diet, the severity of any infection, time of administration and other clinical factors. The dosage may vary with the type of matrix used in the reconstitution and the type or types of bone and-/or cartilage proteins present in the composition The addition of other known growth factors, such as EGF, PDGF, TGF-α, TGF-β, and IGF-I to the final composition, may also effect the dosage.

Progress can be monitored by periodic assessment of cartilage and/or bone growth and/or repair. The progress can be monitored, for example, using x-rays, histomorphometric determinations and tetracycline labeling The following examples illustrate practice of the present invention in recovering and characterizing bovine cartilage and/or bone proteins of the invention and employing these proteins to recover the corresponding human protein or proteins and in expressing the proteins via recombinant techniques.

EXAMPLE I

Isolation of Bovine Cartilage/Bone Inductive Protein

Ground bovine bone powder (20–120 mesh, Helitrex) is prepared according to the procedures of M. R. Urist et.al., *Proc. Natl Acad. Sci USA,* 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 16 hours at 4° C. with 50 liters of 2M $CaCl_2$ and 10mM ethylenediamine-tetraacetic acid EDTA], and followed by extraction for 4 hours in 50 liters of 0.5M EDTA The residue is washed three times with distilled water before its resuspension in 20 liters of 4M guanidine hydrochloride [GuCl], 20mM Tris (pH 7.4), lmM N-ethylmaleimide, lmM iodoacetamide, lmM phenylmethylsulfonyl fluorine as described in *Clin. Orthop. Rel. Res.,* 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50mM Tris, 0.lM NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50mM NaAc, 50mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath - Reddi assay (described in Example III below) desorbed from the column by 50mM NaAc, 0.25mM NaCl, 6M urea (pH 4.6). The protein from this step elution is concentrated 20- to 40-fold, then diluted 5 times with 80mM KP04, 6M urea (pH6.0). The pH of the solution is adjusted to 6.0 with 500mM $K_2HPO_4$. The sample is applied to an hydroxylapatite column (LKB) equilibrated in 80mM $KPO_4$, urea (pH6.0) and all unbound protein is removed by washing the column with the same buffer. Protein having bone and/or cartilage formation activity is eluted with 100mM $KPO_4$ (pH7.4) and 6M urea.

The protein is concentrated approximately 10 times, and solid NaCl added to a final concentration of 0.15M. This material is applied to a heparin—Sepharose column equilibrated in 50mM $KPO_4$, 150mM NaCl, 6M urea (pH7.4). After extensive washing of the column with starting buffer, a protein with bone and/or cartilage inductive activity is eluted by 50mM $KPO_4$, 700mM NaCl, 6M urea (pH7.4). This fraction is concentrated to a minimum volume, and 0.4ml aliquots are applied to Superose 6 and Superose 12 columns connected in series, equilibrated with 4M GuCl, 20mM Tris (pH7.2) and the columns developed at a flow rate of 0.25ml/min. The protein demonstrating bone and/or cartilage inductive activity corresponds to an approximate 30,000 dalton protein.

The above fractions from the superose columns are pooled, dialyzed against 50mM NaAc, 6M urea (pH4.6), and applied to a Pharmacia MonoS HR column. The column is developed with a gradient to 1.0M NaCl, 50mM NaAc, 6M urea (pH4.6). Active bone and/or cartilage formation fractions are pooled. The active material is further fractionated on a MonoQ column. The protein is dialyzed against 6M urea, 25mM diethanolamine, pH 8.6 and then applied to a 0.5 by 5 cm MonoQ column (Pharmacia) which is developed with a gradient of 6M urea, 25mM diethanolamine, pH 8.6 and 0.5 M NaCl, 6M urea, 25mM diethanolamine, pH 8.6. Fractions are brought to pH3.0 with 10% trifluoroacetic acid (TFA). The material is applied to a 0.46×25cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1ml per minute). Active material is eluted at approximately 40-44% acetonitrile. Fractions were assayed for cartilage and/or bone formation activity Aliquots of the appropriate fractions are iodinated by one of the following methods: P. J. McConahey et.al., *Int Arch. Allerov*, 29 185–189 (1966); A. E. Bolton et.al., *Biochem J.*, 133:529 (1973); and D. F. Bowen-Pope, *J. Biol. Chem.*, 237:5161 (1982). The iodinated proteins present in these fractions are analyzed by SDS gel electrophoresis.

EXAMPLE II

Characterization of Bovine Cartilaqe/Bone Inductive Factor

A. Molecular Weight

Approximately 5µg protein from Example I in 6M urea, 25mM diethanolamine, pH 8.6, approximately 0.3 M NaCl is made 0.1% with respect to SDS and dialyzed against 50 mM tris/HCl 0.1% SDS pH 7.5 for 16 hrs. The dialyzed material is then electrophorectically concentrated against a dialysis membrane [Hunkapillar et.al. Meth. *Enzymol*. 91: 227-236 (1983)] with a small amount of I 125 labelled counterpart. This material (volume approximately 100-1) is loaded onto a 12% polyacrylamide gel and subjected to SDS-PAGE [Laemmli, U.K. *Nature*, 227:680–685 (1970)] without reducing the sample with dithiothreitol. The molecular weight is determined relative to prestained molecular weight standards (Bethesda Research Labs). Following autoradiography of the unfixed gel the approximate 28,000-30,000 dalton band is excised and the protein electrophoretically eluted from the gel (Hunkapillar et.al. supra). Based on similar purified bone fractions as described in the co-pending "BMP" applications described above wherein bone and/or cartilage activity is found in the 28,000-30,000 region, it is inferred that this band comprises bone and/or cartilage inductive fractions.

B. Subunit Characterization

The subunit composition of the isolated bovine bone protein is also determined The eluted protein described above is fully reduced and alkylated in 2% SDS using iodoacetate and standard procedures and reconcentrated by electrophoretic packing. The fully reduced and alkylated sample is then further submitted to SDS-PAGE on a 12% gel and the resulting approximate 14,000-20,000 dalton region having a doublet appearance located by autoradiography of the unfixed gel A faint band remains at the 28,000-30,000 region. Thus the 28,000-30,000 dalton protein yields a broad region of 14,000-20,000 which may otherwise also be interpreted and described as comprising two broad bands of approximately 14,000-16,000 and 16,000-18,000 daltons.

EXAMPLE III

Rosen Modified Sampath-Reddi Assay

A modified version of the rat bone formation assay described in Sampath and Reddi, *Proc. Natl. Acad. Sci. U.S. A.*, b 80:6591-6595 (1983) is used to bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1 % TFA, and the resulting solution added to 20mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21-49 day old male Long Evans rats. The implants are removed after 7-14 days. Half of each implant is used for alkaline phosphatase analysis [See, A. H. Reddi et.al., *Proc. Natl Acad Sci.*, 69:1601 (1972)].

The other half of each implant is fixed and processed for histological analysis. Glycolmethacrylate sections (1µm) are stained with Von Kossa and acid fuschin or toluidine blue to score the amount of induced bone and cartilage formation present in each implant The terms +1 through +5 represent the area of each histological section of an implant occupied by new bone and/or cartilage cells and newly formed bone and matrix A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone.

It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of I OD/mg-cm is used as an estimate for protein and the protein is run on SDS PAGE followed by silver staining or radioiodination and autoradiography.

EXAMPLE IV

Bovine BMP-5 Protein Composition

The gel slice of the approximate 14,000–20,000 dalton region described in Example IIB is fixed with methanol-acetic acid-water using standard procedures, briefly rinsed with water, then neutralized with 0.1M ammonium bicarbonate. Following dicing the gel slice with a razor blade, the protein is digested from the gel matrix by adding 0.2 μg of TPCK-treated trypsin (Worthington) and incubating the gel for 16 hr. at 37 degrees centigrade. The resultant digest is then subjected to RPHPLC using a C4 Vydac RPHPLC column and 0.1% TFA-water 0.1% TFA water-acetonitrile gradient. The resultant peptide peaks were monitored by UV absorbance at 214 and 280 nm and subjected to direct amino terminal amino acid sequence analysis using an Applied Biosystems gas phase sequenator (Model 470A). One tryptic fragment is isolated by standard procedures having the following amino acid sequence as represented by the amino acid standard three-letter symbols and where "Xaa" indicates an unknown amino acid the amino acid in parentheses indicates uncertainty in the sequence:

Xaa-His-Glu-Leu-Tyr-Val-Ser-Phe-(Ser)

The following four oligonucleotide probes are designed on the basis of the amino acid sequence of the above-identified tryptic fragment and synthesized on an automated DNA synthesizer.
PROBE #1: GTRCTYGANATRCANTC
PROBE #2: GTRCTYGANATRCANAG
PROBE #3: GTRCTYAAYATRCANTC
PROBE #4: GTRCTYAAYATRCANAG The standard nucleotide symbols in the above identified probes are as follows: A,adenosine; C,cytosine; G,guanine; T,thymine; N, adenosine or cytosine or guanine or thymine; R,adenosine or guanine; and Y,-cytosine or thymine.

Each of the probes consists of pools of oligonucleotides. Because the genetic code is degenerate (more than one codon can code for the same amino acid), a mixture of oligonucleotides is synthesized that contains all possible nucleotide sequences encoding the amino acid sequence of the tryptic. These probes are radioactively labeled and employed to screen a bovine cDNA library as described below Poly(A) containing RNA is isolated by oligo(dT) cellulose chromatography from total RNA isolated from fetal bovine bone cells by the method of Gehron-Robey et.al. in *Current Advances in Skeletogenesis*, Elsevier Science Marion Young, National Institute of Dental Research, National Institutes of Health. A cDNA library is made in lambda gt10 (Toole et.al. supra) and plated on 50 plates at 8000 recombinants per plate. These recombinants (400,000) are screened on duplicate nitrocellulose filters with a comb in ation of Probes 1, 2, 3, and 4 using the Tetramethylammonium chloride (TMAC) hybridization procedure [see Wozney et.al. *Science*, 242: 1528–1534 (1988)]. Twenty-eight positives are obtained and are replated for secondaries. Duplicate nitrocellulose replicas again are made. One set of filters are screened with Probes 1 and 2; the other with Probes 3 and 4. Six positives are obtained on the former, 21 positives with the latter. One of the six, called HEL5, is plague purified, a phage plate stock made, and bacteriophage DNA isolated. This DNA is digested with EcoRI and subcloned into M13 and pSP65. The DNA sequence and derived amino acid sequence of this fragment is shown in Table I.

DNA sequence analysis of this fragment in M13 indicates that it encodes the desired tryptic peptide sequence set forth above, and this derived amino acid sequence is preceded by a basic residue (Lys) as predicted by the specificity of trypsin The underlined portion of the sequence in Table I from amino acid #42 to #48 corresponds to the tryptic fragment identified above from which the oligonucleotide probes are designed The derived amino acid sequence Ser-Gly-Ser-His-Gln-Asp-Ser-Ser-Arg as set forth in Table I from amino acid #15 to #23 is noted to be similar to a tryptic fragment sequence Ser-Thr-Pro-Ala-Gln-Asp-Val-Ser-Arg found in the 28,000–30,000 dalton purified bone preparation as described in the "BMP" co-pending applications mentioned above. This fragment set forth in Table I is a portion of the DNA sequence which encodes a bovine BMP-5 protein of the invention. The DNA sequence indicates an open reading frame from the 5' end of the clone of 420 base pairs, encoding a partial peptide of 140 amino acid residues (the first 7 nucleotides are of the adaptors used in the cloning procedure). An in-frame stop codon (TAA) indicates that this clone encodes the carboxy-terminal part of the bovine BMP-5 cartilage/bone protein of the invention.

TABLE I

1 TCTAGAGGTGAGAGCAGCCAACAAGAGAAAAAATCAAAACCGCAATAAATCCGGCTCTCAT 61
 Leu Glu Val Arg Ala Ala Asn Lys Arg Lys Asn Gln Asn Arg Asn Lys <u>Ser Gly Ser His</u>
 (1)                                                                  (15)

62 CAGGACTCCTCTAGAATGTCCAGTGTTGGAGATTATAACACCAGTGAACAAAAACAAGCC 121
 <u>Gln Asp Ser Ser Arg</u> Met Ser Ser Val Gly Asp Tyr Asn Thr Ser Glu Gln Lys Gln Ala
 (23)

TABLE I-continued

| | | |
|---|---|---|
| 122 | TGTAAAAAGCATGAACTCTATGTGAGTTTCCGGGATCTGGGATGGCAGGACTGGATTATA | 181 |
| | Cys Lys Lys His Glu Leu Tyr Val Ser Phe Arg Asp Leu Gly Trp Gln Asp Trp Ile Ile | |
| | (42) | |
| 182 | GCACCAGAAGGATATGCTGCATTTTATTGTGATGGAGAATGTTCTTTTCCACTCAATGCC | 241 |
| | Ala Pro Glu Gly Tyr Ala Ala Phe Tyr Cys Asp Gly Glu Cys Ser Phe Pro Leu Asn Ala | |
| 242 | CATATGAATGCCACCAATCATGCCATAGTTCAGACTCTGGTTCACCTGATGTTTCCTGAC | 301 |
| | His Met Asn Ala Thr Asn His Ala Ile Val Gln Thr Leu Val His Leu Met Phe Pro Asp | |
| 302 | CACGTACCAAAGCCTTGCTGCGCGACAAACAAACTAAATGCCATCTCTGTGTTGTACTTT | 361 |
| | His Val Pro Lys Pro Cys Cys Ala Thr Asn Lys Leu Asn Ala Ile Ser Val Leu Tyr Phe | |
| 362 | GATGACAGCTCCAATGTCATTTTGAAAAAGTACAGAAATATGGTCGTGCGTTCGTGTGGT | 421 |
| | Asp Asp Ser Ser Asn Val Ile Leu Lys Lys Tyr Arg Asn Met Val Val Arg Ser Cys Gly | |
| 422 | TGCCACTAATAGTGCATAATAATGGTAATAAGAAAAAAGATCTGTATGGAGGTTTATGA | 481 |
| | Cys His End | |
| | (140) | |
| 481 | CTACAATAAAAAATATCTTTCGGATAAAAGGGGAATTTAATAAAATTAGTCTGGCTCATT | 540 |
| 541 | TCATCTCTGTAACCTATGTACAAGAGCATGTATATAGT | 578 |

The remaining positive clones isolated with probes #1, #2, #3, and #4 described above are screened with HEL5 and a further clone is identified that hybridizes under reduced hybridization conditions [5x SSC, 0.1% SDS, 5X Denhardt's, 100 μg/ml salmon sperm DNA standard hybridization buffer (SHB) at 65° C., wash in 2XSSC 0.1% SDS at 65° C.]. This clone is plaque purified, a phage plate stock made and bacteriophage DNA isolated. The DNA sequence and derived amino acid sequence of a portion of this clone is shown in Table II. This sequence represents the DNA sequence encoding a BMP-6 cartilage/bone protein of the invention.

The first underlined portion of the sequence in Table II from amino acid #97 - amino acid #105 corresponds to the lo tryptic fragment found in the 28,000-30,000 dalton purified bovine bone preparation (and its reduced form at approximately 18,000-20,000 dalton reduced form) as described second underlined sequence in Table II from amino acid #124 —amino acid #130 corresponds to the tryptic fragment identified above from which the oligonucleotide probes are designed.

The DNA sequence of Table II indicates an open reading frame of 666 base pairs starting from the 5' end of the sequence of Table II, encoding a partial peptide of 222 amino acid residues. An in-frame stop codon (TGA) indicates that this clone encodes the carboxy-terminal part of a bovine BMP-6 protein of the invention. Based on knowledge of other BMP proteins and other proteins in the TGF-β family, it is predicted that the precursor polypeptide would be cleaved at the three basic residues (ArgArgArg) to yield a mature peptide beginning with residue 90 or 91 of the sequence of Table II.

TABLE II

| 9 | 18 | 27 | 36 | 45 | 54 |
|---|---|---|---|---|---|
| CTG CTG GGC | ACG CGT GCT | GTG TGG GCC | TCA GAG GCG | GGC TGG CTG | GAG TTT GAC |
| Leu Leu Gly | Thr Arg Ala | Val Trp Ala | Ser Glu Ala | Gly Trp Leu | Glu Phe Asp |
| (1) | | | | | |

| 63 | 72 | 81 | 90 | 99 | 108 |
|---|---|---|---|---|---|
| ATC ACG GCC | ACC AGC AAC | CTG TGG GTC | CTG ACT CCG | CAG CAC AAC | ATG GGG CTG |
| Ile Thr Ala | Thr Ser Asn | Leu Trp Val | Leu Thr Pro | Gln His Asn | MET Gly Leu |

| 117 | 126 | 135 | 144 | 153 | 162 |
|---|---|---|---|---|---|
| CAG CTG AGC | GTG GTC ACG | CGT GAT GGG | CTC AGC ATC | AGC CCT GGG | GCC GCG GGC |
| Gln Leu Ser | Val Val Thr | Arg Asp Gly | Leu Ser Ile | Ser Pro Gly | Ala Ala Gly |

| 171 | 180 | 189 | 198 | 207 | 216 |
|---|---|---|---|---|---|
| CTG GTG GGC | AGG GAC GGC | CCC TAC GAC | AAG CAG CCC | TTC ATG GTG | GCC TTC TTC |
| Leu Val Gly | Arg Asp Gly | Pro Tyr Asp | Lys Gln Pro | Phe MET Val | Ala Phe Phe |

| 225 | 234 | 243 | 252 | 261 | 270 |
|---|---|---|---|---|---|
| AAG GCC AGT | GAG GTC CAC | GTG CGC AGT | GCC CGG TCG | GCC CCC GGG | CGG CGC CGG |
| Lys Ala Ser | Glu Val His | Val Arg Ser | Ala Arg Ser | Ala Pro Gly | Arg Arg Arg |

| 279 | 288 | 297 | 306 | 315 | 324 |
|---|---|---|---|---|---|
| CAG CAG GCC | CGG AAC CGC | TCC ACC CCG | GCC CAG GAC | GTG TCG CGG | GCC TCC AGC |
| Gln Gln Ala | Arg Asn Arg | Ser Thr Pro | Ala Gln Asp | Val Ser Arg | Ala Ser Ser |

| 333 | 342 | 351 | 360 | 369 | 378 |
|---|---|---|---|---|---|
| GCC TCA GAC | TAC AAC AGC | AGC GAG CTG | AAG ACG GCC | TGC CGG AAG | CAT GAG CTC |
| Ala Ser Asp | Tyr Asn Ser | Ser Glu Leu | Lys Thr Ala | Cys Arg Lys | His Glu Leu |

| 387 | 396 | 405 | 414 | 423 | 432 |
|---|---|---|---|---|---|
| TAC GTG AGC | TTC CAG GAC | CTG GGG TGG | CAG GAC TGG | ATC ATT GCC | CCC AAG GGC |
| Tyr Val Ser | Phe Gln Asp | Leu Gly Trp | Gln Asp Trp | Ile Ile Ala | Pro Lys Gly |

TABLE II-continued

```
         441         450         459         468         477         486
TAC GCT GCC AAC TAC TGT GAC GGA GAA TGT TCG TTC CCT CTC AAC GCA CAC ATG
Tyr Ala Ala Asn Tyr Cys Asp Gly Glu Cys Ser Phe Pro Leu Asn Ala His MET 495         504         513         522         531         540
AAC GCT ACC AAC CAT GCC ATC GTG CAG ACC CTG GTT CAC CTC ATG AAC CCC GAG
Asn Ala Thr Asn His Ala Ile Val Gln Thr Leu Val His Leu MET Asn Pro Glu 549         558         567         576         585         594
TAC GTC CCC AAA CCG TGC TGC GCG CCC ACG AAA CTG AAC GCC ATC TCG GTG CTC
Tyr Val Pro Lys Pro Cys Cys Ala Pro Thr Lys Leu Asn Ala Ile Ser Val Leu 603         612         621         630         639         648
TAC TTC GAC GAC AAC TCC AAT GTC ATC CTG AAG AAG TAC CGG AAC ATG GTC GTA
Tyr Phe Asp Asp Asn Ser Asn Val Ile Leu Lys Lys Tyr Arg Asn MET Val Val 657         666         676         686         696         706         716
CGA GCG TGT GGG TGC CAC TGACTCGGGG TGAGTGGCTG GGGACGCTGT GCACACACTG CCTGGACTCC
Arg Ala Cys Gly Cys His
                    (222)

726         736         746         756         766         776         786
TGGATCACGT CCGCCTTAAG CCCACAGAGG CCCCCGGGAC ACAGGAGGAG ACCCCGAGGC CACCTTCGGC 796         806         816         826         836         846         856
TGGCGTTGGC CTTTCCGCCC AACGCAGACC CGAAGGGACC CTGTCCGCCC CTTGCTCACA CCGTGAGCGT 866         876         886
TGTGAGTAGC CATCGGGCTC TAGGAAGCAG CACTCGAG
```

When the tryptic sequence His-Glu-Leu-Tyr-Val-Ser-Phe-(Ser) described above was identified, it was noted to be similar to the sequence His-Pro-Leu-Tyr-Val-Asp-Phe-Ser found in the bovine and human cartilage/bone protein BMP-2A sequence described in co-pending U.S. application Ser. No. 179,100. The amino acid sequences of the BMP-5 and BMP-6 polypeptides as set forth in Tables I and II show significant homology to each other, as well as to BMP-2A; the DNA sequences encoding these proteins are also homologous. The carboxy-terminal 102 amino acid residues of bovine BMP-5 and BMP-6 have 89% identity. The DNA sequences of bovine BMP-5 and BMP-6 have approximately 78% sequence similarity. Furthermore, the carboxy-terminal 102 amino acid residues of bovine BMP-5 has 59% sequence identity with the carboxyterminal 101 amino acid residues of human BMP-2A; BMP-6 and BMP-2A have 61% sequence identity over similar regions The DNA sequences of bovine BMP-5 and human BMP-2A are approximately 64% similar; those of bovine BMP-6 and human BMP-2A are 66% similar.

EXAMPLE V

Human BMP-5 Proteins

Human cell lines which synthesize BMP-5 and/or BMP-6 mRNAs are identified in the following manner. RNA is isolated from a variety of human cell lines, selected for poly(A)-containing RNA by chromatography on oligo(dT) cellulose, electrophoresed on a formaldehyde-agarose gel, and transferred to nitrocellulose. A nitrocellulose replica of the gel is hybridized to a single stranded M13 32P-labeled probe corresponding to the above mentioned BMP-5 EcoRI-BglII fragment containing nucleotides 1–465 of the sequence of Table I. A strongly hybridizing band is detected in the lane corresponding to the human osteosarcoma cell line U-20S RNA. Another nitrocellulose replica is hybridized to a single stranded M13 32P-labeled probe containing the PstI-SmaI fragment of bovine BMP-6 (corresponding to nucleotides 106–261 of Table II). It is found that several RNA species in the lane corresponding to U-20S RNA hybridize to this probe.

A cDNA Library is made in the vector lambda ZAP (Stratagene) from U-20S poly(A)-containing RNA using established techniques (Toole et.al.). 750,000 recombinants of this library are plated and duplicate nitrocellulose replicas made. The SmaI fragment of bovine BMP-6 corresponding to nucleotides 259–751 of Table II is labeled by nick-translation and hybridized to both sets of filters in SHB at 65°. One set of filters is washed under stringent conditions (0.2X SSC, 0.1% SDS at 65°), the other under reduced stringency conditions (lX SSC, 0.1% SDS at 65°). Many duplicate hybridizing recombinants (approximately 162) are noted. 24 are picked and replated for secondaries. Three nitrocellulose replicas are made of each plate. One is hybridized to the BMP-6 SmaI probe, one to a nick-translated BMP-6 PstI-SacI fragment (nucleotides 106–378 of Table II), and the third to the nick-translated BMP-5 XbaI fragments (nucleotides 1–76 of Table I). Hybridization and washes are carried out under stringent conditions.

17 clones that hybridized to the third probe more strongly than to the second probe are plaque purified DNA sequence analysis of one of these, U2–16, indicated that it encodes human BMP-5. U2–16 was deposited with the American Type Culture Collection (ATCC), Rockville, MD on Thurs. 22, 1989 under accession number ATCC 68019. A portion of the DNA sequence of this clone is given in Table III. The first 102 nucleotides encode a partial peptide of 34 amino acids, the carboxy-terminus of the protein as evidenced by the stop codon (TAA) following this sequence. The encoded carboxyterminal 32 amino acids are identical to the corresponding residues of the bovine BMP-5 protein given in Table I.

TABLE III

```
         9          18          27
CCA ACC AAA TTA AAT GCC ATC TCT GTT CTG TAC
Pro Thr Lys Leu Asn Ala Ile Ser Val Leu Tyr
(1)
```

TABLE III-continued

```
     36           45           54           63
TTT GAT GAC AGC TCC AAT GTC ATT TTG AAA AAA
Phe Asp Asp Ser Ser Asn Val Ile Leu Lys Lys 72           81           90           99
TAT AGA AAT ATG GTA GTA CGC TCA TGT GGC TGC
Tyr Arg Asn MET Val Val Arg Ser Cys Gly Cys 112          122          132
CAC TAATATTAAA TAATATTGAT AATAACAAAA
His
(34)

142          152          162
AGATCTGTAT TAAGGTTTAT GGCTGCAATA 172          182          192
AAAAGCATAC TTTCAGACAA ACAGAAAAAA AAA
```

The full DNA sequence and derived amino acid sequence of ATCC 68019 is set forth in Table IV below. This clone contains all of the sequence necessary to encode human BMP-5 proteins of the invention.

The cDNA sequence of Table IV contains an open reading frame of 1362 bp, encoding a portein of 454 amino acis, preceded by a 5' untranslated region of 700 pb with stop condons in all frames, and contains a 3' untranslated region of 90 pb following the in frame stop condon (TAA).

This protein of 454 amino acids has a molecular weight of apprxoimately 52,000 kd as predicted by its amino acid sequence, and is contemplated to represent the primary translation product. based on knowledge of other BMP proteins and other proteins within the TGF-β family, it is predicted that the precursor polypeptide would be cleaved at the tribasic peptide Lys-Arg Lyc yielding a 132 amio acid mature peptide.

The underlined sequence of Table IV from amino acid #329 to #337 Ser-Ser-Ser-His-Gln-Asp-Ser-Ser-Arg shares homology with the bovine sequence of Table IV. Each of these sequences shares homology with a tryptic fragment sequence Ser-Thr-Pro-Ala-Gln-Asp-Val-Ser-Arg found in the 28,000-30,000 dalton purified one preparation (and its reduced form at apprxoimately 18,000-20,000 daltons) as described in the "BMP" co-pending applictions metnioned above.

The underlined sequence of Table IV from amino acid #356 to #362 His-Glu-Leu-Tyr-Val-Ser-Phe corresponds to the tryptic fragment identified in the bovine bone preparation described above from which the oligonucleotide probes are designed.

The corresponding bovine and human BMP-5 genes can be isolated using as probes the cDNA sequence set forth in Table I and Table III, respectively.

Additional methods known to those skilled in the art may be used to isolate the genetic material encoding human and other species' cartilage/bone proteins of the invention.

EXAMPLE VI

Expression of the BMP-5 Proteins

In order to produce bovine, human or other mammalian proteins of the invention, the DNA encoding it is transferred into an appropriate expression vector and introduced into mammalian cells or other preferred eukaryotic or prokaryotic hosts by conventional genetic engineering techniques. It is contemplated that the preferred expression system for biologically active recombinant human proteins of the invention will be stably transformed mammalian cells. It is further contemplated that the preferred mammalian cells will be CHO cells. The transformed host cell is cultured and the BMP-5 protein expressed thereby is recovered and purified. The recombinantly expressed BMP-5 proteins are free of proteinaceous materials with which they ordinarily are associated in nature.

In order to express of biologically active human BMP-5 a selected host cell is transformed, using techniques known to those skilled in the art of genetic engineering, with a DNA sequence encoding human BMP-5 protein Such a DNA sequence comprises the DNA sequence from nucleotide #1 to #102 set forth in Table III. The transformed host cells are cultured and the BMP-5 protein comprising the amino acid sequence from amino acid #1 to amino acid #34 set forth in Table III is expressed The expressed protein is recovered, isolated and purified from the culture and culture medium The purified protein is substantially free from other proteinaceous materials with which it is co-produced

TABLE IV

```
         10           20           30           40           50           60           70
CTGGTATATT TGTGCCTGCT GGAGGTGGAA TTAACAGTAA GAAGGAGAAA GGGATTGAAT GGACTTACAG 80           90          100          110          120          130          140
GAAGGATTTC AAGTAAATTC AGGGAAACAC ATTTACTTGA ATAGTACAAC CTAGAGTATT ATTTTACACT 150          160          170          180          190          200          210
AAGACGACAC AAAAGATGTT AAAGTTATCA CCAAGCTGCC GGACAGATAT ATATTCCAAC ACCAAGGTGC 220          230          240          250          260          270          280
AGATCAGCAT AGATCTGTGA TTCAGAAATC AGGATTTGTT TTGGAAAGAG CTCAAGGGTT GAGAAGAACT 290          300          310          320          330          340          350
CAAAAGCAAG TGAAGATTAC TTTGGGAACT ACAGTTTATC AGAAGATCAA CTTTTGCTAA TTCAAATACC 360          370          380          390          400          410          420
AAAGGCCTGA TTATCATAAA TTCATATAGG AATGCATAGG TCATCTGATC AAATAATATT AGCCGTCTTC 430          440          450          460          470          480          490
TGCTACATCA ATGCAGCAAA AACTCTTAAC AACTGTGGAT AATTGGAAAT CTGAGTTTCA GCTTTCTTAG 500          510          520          530          540          550          560
AAATAACTAC TCTTGACATA TTCCAAAATA TTTAAAATAG GACAGGAAAA TCGGTGAGGA TGTTGTGCTC
```

TABLE IV-continued

```
         570         580         590         600         610         620         630
AGAAATGTCA CTGTCATGAA AAATAGGTAA ATTTGTTTTT TCAGCTACTG GGAAACTGTA CCTCCTAGAA 640         650         660         670         680         690         700
CCTTAGGTTT TTTTTTTTTT AAGAGGACAA GAAGGACTAA AAATATCAAC TTTTGCTTTT GGACAAAA 701          710         719         728         737         746         755         764
ATG CAT CTG ACT GTA TTT TTA CTT AAG GGT ATT GTG GGT TTC CTC TGG AGC TGC TGG GTT CTA GTG GGT
MET His Leu Thr Val Phe Leu Leu Lys Gly Ile Val Gly Phe Leu Trp Ser Cys Trp Val Leu Val Gly
(1)

773         782         791         800         809         818         827
TAT GCA AAA GGA GGT TTG GGA GAC AAT CAT GTT CAC TCC AGT TTT ATT TAT AGA AGA CTA CGG AAC
Tyr Ala Lys Gly Gly Leu Gly Asp Asn His Val His Ser Ser Phe Ile Tyr Arg Arg Leu Arg Asn 836         845         854         863         872         881         890         899
CAC GAA AGA CGG GAA ATA CAA AGG GAA ATT CTC TCT ATC TTG GGT TTG CCT CAC AGA CCC AGA CCA
His Glu Arg Arg Glu Ile Gln Arg Glu Ile Leu Ser Ile Leu Gly Leu Pro His Arg Pro Arg Pro 908         917         926         935         944         953         962
TTT TCA CCT GGA AAA ATG ACC AAT CAA GCG TCC TCT GCA CCT CTC TTT ATG CTG GAT CTC TAC AAT GCC
Phe Ser Pro Gly Lys MET Thr Asn Gln Ala Ser Ser Ala Pro Leu Phe MET Leu Asp Leu Tyr Asn Ala 971         980         989         998         1007        1016        1025        1034
GAA GAA AAT CCT GAA GAG TCG GAG TAC TCA GTA AGG GCA TCC TTG GCA GAA GAG ACC AGA GGG GCA
Glu Glu Asn Pro Glu Glu Ser Glu Tyr Ser Val Arg Ala Ser Leu Ala Glu Glu Thr Arg Gly Ala 1043        1052        1061        1070        1079        1088        1097
AGA AAG GGA TAC CCA GCC TCT CCC AAT GGG TAT CCT CGT CGC ATA CAG TTA TCT CGG ACG ACT CCT
Arg Lys Gly Tyr Pro Ala Ser Pro Asn Gly Tyr Pro Arg Arg Ile Gln Leu Ser Arg Thr Thr Pro 1106        1115        1124        1133        1142        1151        1160        1169
CTG ACC ACC CAG AGT CCT CCT CTA GCC AGC CTC CAT GAT ACC AAC TTT CTG AAT GAT GCT GAC ATG GTC
Leu Thr Thr Gln Ser Pro Pro Leu Ala Ser Leu His Asp Thr Asn Phe Leu Asn Asp Ala Asp MET Val 1178        1187        1196        1205        1214        1223        1232
ATG AGC TTT GTC AAC TTA GTT GAA AGA GAC AAG GAT TTT TCT CAC CAG CGA AGG CAT TAC AAA GAA
MET Ser Phe Val Asn Leu Val Glu Arg Asp Lys Asp Phe Ser His Gln Arg Arg His Tyr Lys Glu 1241        1250        1259        1268        1277        1286        1295
TTT CGA TTT GAT CTT ACC CAA ATT CCT CAT GGA GAG GCA GTG ACA GCA GCT GAA TTC CGG ATA TAC
Phe Arg Phe Asp Leu Thr Gln Ile Pro His Gly Glu Ala Val Thr Ala Ala Glu Phe Arg Ile Tyr 1304        1313        1322        1331        1340        1349        1358        1367
AAG GAC CGG AGC AAC AAC CGA TTT GAA AAT GAA ACA ATT AAG ATT AGC ATA TAT CAA ATC ATC AAG
Lys Asp Arg Ser Asn Asn Arg Phe Glu Asn Glu Thr Ile Lys Ile Ser Ile Tyr Gln Ile Ile Lys 1376        1385        1394        1403        1412        1421        1430
GAA TAC ACA AAT AGG GAT GCA GAT CTG TTC TTG TTA GAC ACA AGA AAG GCC CAA GCT TTA GAT GTG
Glu Tyr Thr Asn Arg Asp Ala Asp Leu Phe Leu Leu Asp Thr Arg Lys Ala Gln Ala Leu Asp Val 1439        1448        1457        1466        1475        1484        1493
GGT TGG CTT GTC TTT GAT ATC ACT GTG ACC AGC AAT CAT TGG GTG ATT AAT CCC CAG AAT AAT TTG
Gly Trp Leu Val Phe Asp Ile Thr Val Thr Ser Asn His Trp Val Ile Asn Pro Gln Asn Asn Leu 1502        1511        1520        1529        1538        1547        1556        1565
GGC TTA CAG CTC TGT GCA GAA ACA GGG GAT GGA CGC AGT ATC AAC GTA AAA TCT GCT GGT CTT GTG
Gly Leu Gln Leu Cys Ala Glu Thr Gly Asp Gly Arg Ser Ile Asn Val Lys Ser Ala Gly Leu Val 1574        1583        1592        1601        1610        1619        1628
GGA AGA CAG GGA CCT CAG TCA AAA CAA CCA TTC ATG GTG GCC TTC TTC AAG GCG AGT GAG GTA CTT
Gly Arg Gln Gly Pro Gln Ser Lys Gln Pro Phe MET Val Ala Phe Phe Lys Ala Ser Glu Val Leu 1637        1646        1655        1664        1673        1682        1691
CTT CGA TCC GTG AGA GCA GCC AAC AAA CGA AAA AAT CAA AAC CGC AAT AAA TCC AGC TCT CAT CAG
Leu Arg Ser Val Arg Ala Ala Asn Lys Arg Lys Asn Gln Asn Arg Asn Lys <u>Ser  Ser  Ser  His  Gln</u>
                                                                                  (329)

1700        1709        1718        1727        1736        1745        1754        1763
GAC TCC TCC AGA ATG TCC AGT GTT GGA GAT TAT AAC ACA AGT GAG CAA AAA CAA GCC TGT AAG AAG
<u>Asp Ser Ser Arg</u> MET Ser Ser Val Gly Asp Tyr Asn Thr Ser Glu Gln Lys Gln Ala Cys Lys Lys
         (337)

1772        1781        1790        1799        1808        1817        1826
CAC GAA CTC TAT GTG AGC TTC CGG GAT CTG GGA TGG CAG GAC TGG ATT ATA GCA CCA GAA GGA TAC
<u>His Glu Leu Tyr Val Ser Phe</u> Arg Asp Leu Gly Trp Gln Asp Trp Ile Ile Ala Pro Glu Gly Tyr
(356)        (362)
```

TABLE IV-continued

| 1835 | 1844 | 1853 | 1862 | 1871 | 1880 | 1889 | 1898 |
|------|------|------|------|------|------|------|------|
| GCT | GCA TTT | TAT TGT | GAT GGA | GAA TGT | TCT TTT CCA | CTT AAC GCC | CAT ATG AAT GCC ACC AAC CAC GCT |
| Ala | Ala Phe | Tyr Cys | Asp Gly | Glu Cys | Ser Phe Pro | Leu Asn Ala | His MET Asn Ala Thr Asn His Ala |

| 1907 | 1916 | 1925 | 1934 | 1943 | 1952 | 1961 |
|------|------|------|------|------|------|------|
| ATA GTT CAG | ACT CTG GTT | CAT CTG ATG | TTT CCT GAC | CAC GTA CCA | AAG CCT TGT | TGT GCT CCA ACC AAA |
| Ile Val Gln | Thr Leu Val | His Leu MET | Phe Pro Asp | His Val Pro | Lys Pro Cys | Cys Ala Pro Thr Lys |

| 1970 | 1979 | 1988 | 1997 | 2006 | 2015 | 2024 | 2033 |
|------|------|------|------|------|------|------|------|
| TTA AAT GCC | ATC TCT GTT | CTG TAC TTT | GAT GAC AGC | TCC AAT GTC | ATT TTG AAA | AAA TAT AGA | AAT ATG |
| Leu Asn Ala | Ile Ser Val | Leu Tyr Phe | Asp Asp Ser | Ser Asn Val | Ile Leu Lys | Lys Tyr Arg | Asn MET |

| 2042 | 2051 | 2060 | 2070 | 2080 | 2090 | 2100 |
|------|------|------|------|------|------|------|
| GTA GTA CGC | TCA TGT GGC | TGC CAC | TAATATTAAA | TAATATTGAT | AATAACAAAA | AGATCTGTAT |
| Val Val Arg | Ser Cys Gly | Cys His (450) | | | | |

| 2110 | 2120 | 2130 | 2140 | 2150 |
|------|------|------|------|------|
| TAAGGTTTAT | GGCTGCAATA | AAAAGCATAC | TTTCAGACAA | ACAGAAAAAA AAA |

One skilled in the art can construct mammalian expression vectors by employing the DNA sequences of the invention sequences and known vectors, such as pCD [Okayama et.al., *Mol. Cell Biol.*, 2:161-170 (1982)] and pJL3, pJL4 [Gough et.al., *EMBO J.*, 4:645-653 (1985)]. The transformation of these vectors into appropriate host cells may result in expression of the proteins of the invention. One skilled in the art could manipulate the sequences of the invention by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-from or altering nucleotides therein by other known techniques). The modified coding sequence could then be inserted into a known bacterial vector using procedures such as described in T. Taniguchi et.al., *Proc. Natl Acad. Sci. USA.* 77:5230-5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a protein of the invention from mammalian cells involves the construction of cells containing multiple copies of the heterologous gene encoding proteins of the invention. The heterologous gene may be linked to an ampl ifiable marker, e.g. the dihydrofolate reductase (DHFR) gene for which cells containing increased gene copies can be selected for propagation in increasing concentrations of methotrexate (MTX) according to the procedures of Kaufman and Sharp, J. *Mol. Biol.*, 159:601-629 (1982). This approach can be employed with a number of different cell types. For example, a plasmid containing a DNA sequence for a protein of the invention in operative association with other plasmid sequences enabling expression thereof and the DHFR expression plasmid pAdA26SV(A)3 [Kaufman and Sharp, Mol. *Cell. Biol.*, 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5uM MTX) as described in Kaufman et.al., *Mol Cell Biol.* 5:1750 (1983). Protein expression should increase with increasing levels of MTX resistance. Transformants are cloned, and the proteins of the invention are recovered, isolated, and purified from the culture medium. Biologically active protein expression is monitored by the Rosen-modified Sampath - Reddi rat bone formation assay described above in Example III. Similar procedures can be followed to produce other related proteins

EXAMPLE VII

Bioloqical Activity of Expressed BMP-5 Proteins

To measure the biological activity of the expressed BMP-5 proteins obtained in Example VI above, the BMP-5 proteins are recovered from the culture media and purified. BMP-5 may be partially purified on a Heparin Sepharose column. 4 ml of the collected post transfection conditioned medium supernatant from one 100 mm culture dish is concentrated approximately 10 fold by ultrafiltration on a YM membrane and then dialyzed against 20mM Tris, 0.15 M NaCl, pH 7.4 (starting buffer). This material is then applied to a 1.1 ml Heparin Sepharose column in starting buffer. Unbound proteins are removed by an 8 ml wash of starting buffer, and bound proteins, including proteins of the invention, are desorbed by a 3-4 ml wash of 20 mM Tris, 2.0 M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-5 proteins of the invention have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Levels of activity may also be tested for host cell extracts. Partial purification is accomplished in a similar manner as described above except that 6 M urea is included in all the buffers The procedures described above may be employed to isolate other related proteins of interest by utilizing the bovine or human proteins as a probe source. Such other proteins may find similar utility in, inter alia, fracture repair, wound healing and tissue repair.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated DNA molecule having a sequence encoding a BMP-5 protein which is characterized by the ability to induce the formation of cartilage and/or bone said DNA comprising the DNA sequence selected from the group consisting of
    (a) nucleotide #1 to #102 of FIG. 3;
    (b) nucleotide #1665 to #2060 of FIG. 4;
    (c) nucleotide #699 to #2060 of FIG. 4; and
    (d) naturally occurring allelic sequences and equivalent degenerative condon sequences of (a), (b), and (c).

2. A host cell transfomred with a DNA of claim 1.

3. A vector comprising a DNA sequence of claim 1 in operative association with an expressio control sequence therefor.

4. A host cell transformed with a vector of claim 3.

* * * * *